US009855430B2

(12) United States Patent
Ghosh et al.

(10) Patent No.: US 9,855,430 B2
(45) Date of Patent: Jan. 2, 2018

(54) FAR-FIELD P-WAVE SENSING IN NEAR REAL-TIME FOR TIMING DELIVERY OF PACNG THERAPY IN A CARDIAC MEDICAL DEVICE AND MEDICAL DEVICE SYSTEM

(71) Applicant: Medtronic, Inc., Minneapolis, MN (US)

(72) Inventors: Subham Ghosh, Blaine, MN (US); Kushagr Gupta, Stanford, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/926,359

(22) Filed: Oct. 29, 2015

(65) Prior Publication Data

US 2017/0120058 A1    May 4, 2017

(51) Int. Cl.
| | |
|---|---|
| *A61N 1/00* | (2006.01) |
| *A61N 1/365* | (2006.01) |
| *A61N 1/368* | (2006.01) |
| *A61N 1/37* | (2006.01) |
| *A61N 1/372* | (2006.01) |
| *A61N 1/39* | (2006.01) |

(52) U.S. Cl.
CPC ......... *A61N 1/36514* (2013.01); *A61N 1/368* (2013.01); *A61N 1/3702* (2013.01); *A61N 1/37288* (2013.01); *A61N 1/3956* (2013.01)

(58) Field of Classification Search
USPC ...................................................... 607/4, 17
See application file for complete search history.

(56) References Cited

U.S. PATENT DOCUMENTS 5,354,316 A   10/1994   Keimel
5,545,186 A    8/1996   Olson et al.
(Continued)

FOREIGN PATENT DOCUMENTS

WO   2015109071 A1   7/2015

OTHER PUBLICATIONS (PCT/US2016/059076) PCT Notification of Transmittal of the International Search Report and the Written Opinion of the International Searching Authority, dated Jan. 25, 2017, 12 pages.

*Primary Examiner* — Nicole F Johnson

(57) ABSTRACT

A medical device system for controlling ventricular pacing therapy during cardiac resynchronization therapy that includes a sensing device to sense a cardiac signal and emit a trigger signal in response to the sensed cardiac signal, a therapy delivery device to deliver the ventricular pacing in response to the emitted trigger signal, and a processor configured to identify a fiducial point of the cardiac signal sensed in real-time, set a window comprising a start point positioned a first distance prior to the fiducial point and an endpoint positioned a second distance less than the first distance subsequent to the fiducial point, determine a signal characteristic of the cardiac signal within the window, determine whether a P-wave is detected in response to the signal characteristic, determine whether an atrio-ventricular interval timer has expired, and emit a trigger signal to deliver the ventricular pacing timed off of the local maximum in response to the P-wave being detected and not timed off of the local maximum in response to the timer being expired.

19 Claims, 7 Drawing Sheets

(56) References Cited

U.S. PATENT DOCUMENTS

| | | | |
|---|---|---|---|
| 5,855,593 | A | 1/1999 | Olson et al. |
| 6,393,316 | B1 | 5/2002 | Gillberg et al. |
| 7,742,812 | B2 | 6/2010 | Ghanem et al. |
| 7,904,153 | B2 | 3/2011 | Greenhut et al. |
| 8,160,684 | B2 | 4/2012 | Ghanem et al. |
| 8,532,785 | B1 | 9/2013 | Crutchfield et al. |
| 2009/0299203 | A1 | 12/2009 | De Voir et al. |
| 2013/0165983 | A1* | 6/2013 | Ghosh ................ A61N 1/3706 607/4 |
| 2014/0323893 | A1* | 10/2014 | Ghosh ................ A61B 5/044 600/510 |
| 2015/0032173 | A1 | 1/2015 | Ghosh |
| 2015/0157231 | A1 | 6/2015 | Gillberg et al. |
| 2015/0321011 | A1 | 11/2015 | Carney et al. |
| 2015/0321012 | A1 | 11/2015 | Cinbis et al. |

\* cited by examiner

FAR-FIELD P-WAVE SENSING IN NEAR REAL-TIME FOR TIMING DELIVERY OF PACNG THERAPY IN A CARDIAC MEDICAL DEVICE AND MEDICAL DEVICE SYSTEM

FIELD OF THE DISCLOSURE

The present disclosure pertains to cardiac pacing methods and systems, and, more particularly, to a medical device and medical device system for sensing a P-wave for controlling delivery of a pacing therapy during a cardiac resynchronization therapy.

BACKGROUND OF THE DISCLOSURE

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, leadless intracardiac pacemakers have been introduced which can be implanted directly in a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of a leadless, intracardiac pacemaker.

New challenges arise, however, in controlling an intracardiac pacemaker to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in whom one or more heart chambers are electrically paced to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g., an atrio-ventricular (AV) interval and/or an inter-ventricular (VV) interval. The AV interval controls the timing of ventricular pacing pulses relative to a preceding atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

Cardiac resynchronization utilizing cardiac pacing therapy and cardiac pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. In order to ensure the desired evoked response takes place, it is desirable to time the delivery of the ventricular pacing therapy so as to be delivered at a point in time subsequent to a P-wave, resulting in the delivery of the ventricular pacing coinciding with the occurrence of an R-wave of the cardiac cycle of the patient. As a result, the ability to sense P-waves is an important factor in determining timing of the ventricular pacing therapy for cardiac resynchronization therapy (CRT). Furthermore, when either a subcutaneous device or far-field signals are utilized, the R-waves and T-waves of the cardiac cycle are often either only slightly larger or of comparable magnitudes as P-waves, making distinguishing P-waves from R-waves and T-waves even more difficult. Therefore, what is needed is an improved method of distinguishing P-waves of a cardiac cycle for timing of delivery of ventricular pacing during CRT therapy.

DETAILED DESCRIPTION OF EXEMPLARY EMBODIMENTS

In the following detailed description, references are made to illustrative embodiments for carrying out methods of delivering atrial synchronous pacing with sensing of atrial activity from subcutaneous or far-field signals reflecting electrical activity of the different heart chambers. It is understood that other embodiments may be utilized without departing from the scope of the invention. For example, the invention is disclosed in detail herein in the context of a bi-ventricular or multi-electode/multi-site cardiac resynchronization therapy (CRT) delivery.

Exemplary methods, devices, and systems shall be described with reference to FIGS. 1-5. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

Figure 1:
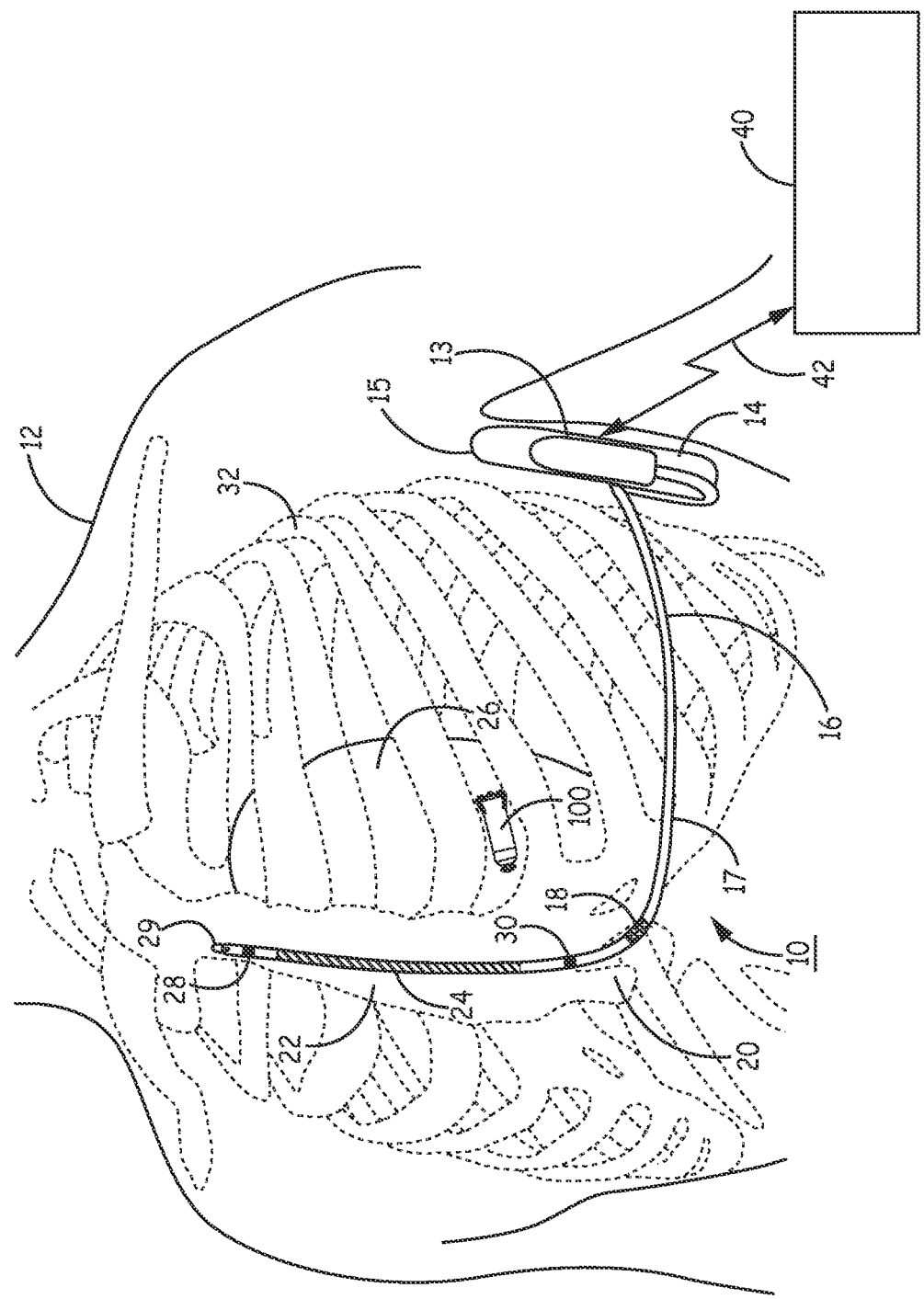
FIG. 1 is a conceptual diagram illustrating an implantable medical device (IMD) system that may be used to sense cardiac electrical signals in patient and provide therapy to the patient's heart.

FIG. 1 is a conceptual diagram illustrating an implantable medical device (IMD) system that may be used to sense cardiac electrical signals in patient and provide therapy to the patient's heart. As illustrated in FIG. 1, an implantable medical device (IMD) system 10 for confirming sensed atrial events for pacing and resynchronization therapy may include a therapy delivery device 100, such as an intracardiac pacemaker and a cardiac sensing device 14, such as a subcutaneous cardiac defibrillator coupled to an extravascular lead 16, such as a subcutaneous device implanted subcutaneously on the left side of a patient 12. Such a medical device system 10 is described, for example, in commonly assigned U.S. patent application Ser. No. 14/695,004, incorporated herein by reference in it's entirety. While the subcutaneous device is shown implanted subcutaneously on the left side of a patient 12, it is understood that sensing device 14 and lead 16 may be implanted at other locations, such as the right side of patient 12, for example. The cardiac sensing device 14 includes a defibrillation lead 16 having a defibrillation electrode 24 positioned along a proximal end of the lead 16, which may be an elongated coil electrode, a pair of sensing electrodes 28 and 30, illustrated as ring electrodes, although other electrode configurations may be utilized, and a trigger signal emitting device 18. Trigger signal emitting device 18 includes a transducer that is controlled by cardiac sensing device 14 to emit trigger signals received by therapy delivery device 100 to cause therapy delivery device 100 to deliver one or more pacing pulses.

Defibrillation lead 16, which is connected to cardiac sensing device 14, extends medially from cardiac sensing device 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is over sternum 22 or offset laterally to the left or right side of the body of sternum 22, and may be implanted subcutaneously, e.g., between the skin and the ribs or sternum. Defibrillation lead 16 may be implanted at other locations or angles relative to sternum 22, or positioned further superior or inferior, depending on the location of cardiac sensing device 14, position of electrodes 24, 28, and 30 and trigger signal emitting device 18 along lead 16, the location of pacemaker 100, or other factors. In other instances, lead 16 may be implanted at other extravascular locations. In one example, lead 16 may be implanted at least partially in a substernal location or within ribcage 32, within the thoracic cavity, and within or outside the pericardium, not necessarily in direct contact with heart 26.

Defibrillation lead 16 is placed along sternum 22 such that a therapy vector between defibrillation electrode 24 and a second electrode (such as a portion of the housing 15 of cardiac sensing device 14 or an electrode placed on a second lead) is substantially across one or both ventricles of heart 26. The therapy vector may, in one example, be viewed as a line that extends from a point on the defibrillation electrode 24 to a point on the housing 15 (sometimes referred to as "can electrode") of cardiac sensing device 14. In another example, defibrillation lead 16 may be placed along sternum 22 such that a therapy vector between defibrillation electrode 24 and housing 15 of cardiac sensing device 14 (or other electrode) is substantially across an atrium of heart 26. In this case, system 10 may be used to provide atrial therapies, such as therapies to treat atrial fibrillation.

Trigger signal emitting device 18 is positioned to establish a trigger signal transmission pathway that does not excessively attenuate the trigger signal transmitted from emitting device 18 to a receiver or detector included in intracardiac therapy delivery device 100. For example, the location of emitting device 18 may be selected so that a direct pathway between emitting device 18 and therapy delivery device 100 avoids, as much as possible, tissues that are highly reflective, scattering or absorbing of the type of trigger signal being used. When lead 16 is positioned extra-thoracically, emitting device 18 may be positioned inferior to the xyphoid process 20 in a position approximately as shown. Emitting device 18 is positioned relative to therapy delivery device 100 to establish an efficient trigger signal transmission pathway, which may be a direct or indirect pathway that takes into account the trigger signal properties and the transmission or attenuation properties of the surrounding and intervening tissues for the type of trigger signal being used.

Defibrillation lead 16 may include an attachment feature 29 at or toward the distal end of lead 16. The attachment feature 29 may be a loop, link, or other attachment feature useful to aid in implantation of lead 16 and/or for securing lead 16 to a desired implant location. In some instances, defibrillation lead 16 may include a fixation mechanism in addition to or instead of the attachment feature 29. For example, defibrillation lead 16 may include a suture sleeve or other fixation mechanism (not shown) located proximal to electrode 30 or near emitting device 18 that is configured to fixate lead 16 near the xiphoid process 20 or lower sternum location. The fixation mechanism (e.g., suture sleeve or other mechanism) may be integral to the lead or may be added by the user prior to implantation. The fixation mechanism may be used to stably locate emitting device 18 inferior to the xyphoid process 20, along an intercostal space, or other desired location to prevent rotation or shifting of the emitting device 18 that may cause trigger signal misdirection or trigger signal loss due to interference or attenuation by body tissues.

Although cardiac sensing device 14 is illustrated as being implanted near a midaxillary line of patient 12, cardiac sensing device 14 may also be implanted at other subcutaneous locations on patient 12, such as further posterior on the torso toward the posterior axillary line, further anterior on the torso toward the anterior axillary line, in a pectoral region, or at other locations of patient 12. In instances in which cardiac sensing device 14 is implanted pectorally, lead 16 would follow a different path, e.g., across the upper chest area and inferior along sternum 22. When the cardiac sensing device 14 is implanted in the pectoral region, the system 10 may include a second lead including a defibrillation electrode, and optionally a trigger signal emitting device, that extends along the left side of the patient such that the defibrillation electrode of the second lead is located along the left side of the patient to function as an anode or cathode of the therapy vector for defibrillating heart 26.

Cardiac sensing device 14 includes a housing 15 that forms a hermetic seal that protects components within cardiac sensing device 14. The housing 15 of cardiac sensing device 14 may be formed of a conductive material, such as titanium or other biocompatible conductive material or a combination of conductive and non-conductive materials. Housing 15 may enclose one or more components, including processors, memories, transmitters, receivers, sensors, sensing circuitry, therapy circuitry and other appropriate components (often referred to herein as modules). In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

Cardiac sensing device 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing 15. Depending on the intended implant location of cardiac sensing device 14, a trigger signal emitting device may be included in connector assembly 13 and/or housing 15 in addition to or in place of the emitting device 18 carried by lead 16 for transmitting trigger signals to therapy delivery device 100.

Lead 16 includes a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly 13 of cardiac sensing device 14. The lead body 17 of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

Defibrillation lead 16 includes elongated electrical conductors (not illustrated) that extend within the elongated lead body 17 from the connector on the proximal end of defibrillation lead 16 to the respective electrodes 24, 28 and 30 and emitting device 18. Although defibrillation lead 16 is illustrated as including three electrodes 24, 28 and 30, defibrillation lead 16 may include more or fewer electrodes. When the connector at the proximal end of defibrillation lead 16 is connected to connector assembly 13, the respective conductors electrically couple to circuitry of cardiac sensing device 14, such as a therapy delivery module, a sensing module, or trigger signal drive signal circuit, via connections in connector assembly 13, including associated feedthroughs.

The electrical conductors transmit electrical stimulation pulses from a therapy module within cardiac sensing device 14 to one or more of electrodes 24, 28 and 30 and transmit sensed electrical signals from one or more of electrodes 24, 28 and 30 to the sensing module within cardiac sensing device 14. An electrical conductor extending from the proximal lead connector to emitting device 18 conducts an electrical control signal to emitting device 18 to cause emitting device 18 to emit a trigger signal at appropriate times for causing intracardiac therapy delivery device 100 to deliver one or more pacing pulses to heart 26.

Cardiac sensing device 14 may sense electrical activity of heart 26 via one or more sensing vectors that include combinations of electrodes 28 and 30 and housing 15. For example, cardiac sensing device 14 may obtain cardiac electrical signals sensed using a sensing vector between electrodes 28 and 30, between electrode 28 and the conductive housing 15, between electrode 30 and the conductive housing 15, or any combination thereof. In some instances, cardiac sensing device 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15 of cardiac sensing device 14.

Cardiac sensing device 14 determines a need for pacing therapy in response to the sensed cardiac electrical signals, which may include P-waves and R-waves for example, and controls emitting device 18 to emit trigger signals based on that determination. The need for pacing pulses may be determined according to programmed single chamber, dual chamber or multi-chamber bradycardia or CRT control parameters or other cardiac pacing therapy parameters.

Cardiac sensing device 14 may also analyze the sensed electrical signals to detect tachyarrhythmia, such as ventricular tachycardia or ventricular fibrillation, and in response to detecting tachyarrhythmia may generate and deliver an electrical stimulation therapy to heart 26. For example, cardiac sensing device 14 may deliver one or more defibrillation shocks via a therapy vector that includes defibrillation electrode 24 of defibrillation lead 16 and the housing 15.

Electrodes 24, 28, 30 and housing 50 may be used for sensing ECG signals for use in controlling the timing of an R-wave synchronized shock delivered by cardiac sensing device 14 and for controlling timing of pacing pulses delivered by therapy delivery device 100. In some instances, one or more pacing therapies may be delivered prior to or after delivery of a defibrillation shock by cardiac sensing device 14, such as anti-tachycardia pacing (ATP) or post shock pacing. In these instances, cardiac sensing device 14 may generate and deliver pacing pulses via therapy vectors that include electrodes 24, 28, 30 and/or housing 15. Alternatively, cardiac sensing device 14 causes trigger signal emitting device 18 to emit trigger signals to cause therapy delivery device 100 to deliver pacing pulses to heart 26 at appropriate times when ATP or post-shock pacing is needed as well as when bradycardia or CRT pacing therapy is needed.

The exemplary cardiac sensing device 14 illustrated in FIG. 1 is illustrative in nature and should not be considered limiting of the sensing device used in a triggered therapy delivery system and associated techniques described in this disclosure. For instance, in addition to sensing ECG signals, cardiac sensing device 14 may include shock therapy capabilities only without pacing therapy capabilities. In other examples, cardiac sensing device 14 may be coupled to more than one lead for sensing ECG signals and/or sending trigger signals to therapy delivery device 100. In still other examples, a sensing device may be substituted for cardiac sensing device 14 that is a single chamber or dual chamber subcutaneous pacemaker without cardioversion/defibrillation capabilities or a sensing-only device without therapy delivery capabilities. Any of these sensing devices may be coupled to housing-based electrodes and/or electrodes carried by a transvenous, intracardiac or extravascular, extracardiac lead for sensing a cardiac electrical signal and determining appropriate times for triggering therapy delivery device 100 to delivery therapy. In another embodiment, the sensing device may be a subcutaneously implanted leadless device, such as the leadless subcutaneous sensor device in commonly assigned U.S. patent application Ser. No. 14/695,004 to Carnet et. al, Ser. No. 14/695,013 to Cinbis et. al, for example, both incorporated by reference in their entireties.

Therapy delivery device 100 may be a transcatheter intracardiac pacemaker adapted for implantation wholly within a heart chamber, e.g., wholly within the RV, wholly within the LV, wholly within the right atrium (RA) or wholly within the left atrium (LA) of heart 26. In the example of FIG. 1, therapy delivery device 100 is positioned proximate to an inner wall of the LV to provide left ventricular pacing. In other examples, therapy delivery device 100 is positioned proximate to an inner wall of the right ventricle to provide right ventricular pacing. In other examples, therapy delivery device 100 may be positioned at any other location outside or within heart 26, including epicardial locations. For example, therapy delivery device 100 may be positioned outside or within the right atrium or left atrium, e.g., to provide respective right atrial or left atrial pacing. In other embodiments, therapy delivery device 100 may be embodied as a therapy delivery device for delivering an electrical stimulation therapy at another body location. Therapy delivery device 100 is shown as a leadless device in FIG. 1. It is contemplated, however that in other embodiments therapy delivery device 100 may be coupled to a lead extending from therapy deliver device 100 to position therapy delivery electrodes at a location spaced apart from therapy delivery device 100.

Depending on the implant location, therapy delivery device 100 may be configured to deliver an electrical stimulation therapy to target therapy site(s) other than the myocardium. For example, therapy delivery device 100 may provide atrioventricular nodal stimulation, fat pad stimulation, vagal stimulation, or other types of neurostimulation. In other examples, system 10 may include a plurality of pacemakers 100, e.g., to deliver electrical stimulation therapy at multiple sites of heart 26 such as within multiple heart chambers for multi-chamber pacing therapies.

Therapy delivery device 100 is capable of producing electrical stimulation pulses delivered to heart 26 via one or more electrodes on the outer housing of therapy delivery device 100. Therapy delivery device 100 includes a receiving transducer for receiving a trigger signal emitted by emitting device 18. In response to detecting the trigger signal, therapy delivery device 100 delivers one or more pacing pulses.

In one embodiment, therapy delivery device 100 includes a pulse generator configured to deliver one or more pacing pulses upon receiving the trigger signal from emitting device 18. Cardiac signal sensing is performed by cardiac sensing device 14. Cardiac sensing device 14 senses ECG signals through lead 16 and controls pacing delivered by therapy delivery device 100 via trigger signals emitted by emitting device 18 under the control of cardiac sensing device 14.

Since therapy delivery device 100 may have no or limited sensing capabilities, therapy delivery device 100 may be "blinded" to intrinsic events, such as intrinsic R-waves, occurring in the same heart chamber and to paced or intrinsic events occurring in other heart chambers. Delivery of CRT, dual chamber pacing, or other multi-chamber pacing therapies may require delivering a pacing pulse at a predetermined time interval after an event, sensed or paced, in another heart chamber. As such, emitting device 18 provides a trigger signal to therapy delivery device 100 in response to ECG signals sensed by cardiac sensing device 14 to cause pacing pulses to be delivered by therapy delivery device 100 at desired time intervals relative to other heart chamber events. Therapy delivery device 100 (for generating pacing pulses) combined with cardiac sensing device 14 (for sensing physiological signals and making therapy delivery decisions) provides the functionality required to deliver various therapies that may require synchronization or coordination with cardiac events occurring in the same or a different heart chamber without physical connection between therapy delivery device 100 and cardiac sensing device 14 implanted at separate implant sites.

FIG. 1 further depicts programmer 40 in wireless communication with cardiac sensing device 14 via communication link 42. In some examples, programmer 40 comprises a handheld computing device, computer workstation, or networked computing device. Programmer 40 includes a user interface that presents information to and receives input from a user. It should be noted that the user may also interact with programmer 40 remotely via a networked computing device.

A user, such as a physician, technician, surgeon, electrophysiologist, other caregiver, or patient, interacts with programmer 40 to communicate with cardiac sensing device 14. For example, the user may interact with programmer 40 to retrieve physiological or diagnostic information from cardiac sensing device 14. A user may also interact with programmer 40 to program cardiac sensing device 14, e.g., select values for operational parameters of the cardiac sensing device 14, including parameters used to control trigger signal emitting device 18 for controlling therapy delivery device 100. A user may use programmer 40 to retrieve information from cardiac sensing device 14 regarding the rhythm of heart 26, heart rhythm trends over time, or arrhythmic episodes.

As indicated, cardiac sensing device 14 and programmer 40 communicate via wireless communication. Examples of communication techniques may include low frequency or radiofrequency (RF) telemetry, but other techniques may be used. In some examples, programmer 40 may include a programming head that is placed proximate to the patient's body near the cardiac sensing device 14 implant site in order to improve the quality or security of communication between cardiac sensing device 14 and programmer 40.

The embodiment illustrated in FIG. 1 is an example configuration of an IMD system 10 and should not be considered limiting of the techniques described herein. In other embodiments, cardiac sensing device 14 may be coupled to a transvenous intracardiac lead extending into the right ventricle (RV) for positioning RV sensing and pacing electrodes and a defibrillation coil electrode within the RV. An example of an RV lead that could be adapted to carry an emitting device 18 is generally disclosed in commonly-assigned, U.S. Pat. No. 5,545,186 (Olson, et al.). In this example, emitting device 18 may be positioned more distally than the position shown on lead 16 such that the emitting device 18 is positioned in the RV, opposite therapy delivery device 100 in the LV. Emitting device 18 may then be enabled to emit a trigger signal from the RV to the therapy delivery device 100 in the LV to coordinate timing of the LV pacing pulse relative to a right atrial event or a right ventricular event. It is contemplated that numerous configurations of a lead-based emitting device 18 may be conceived and emitting device 18 may be positioned along the lead body 17 at relatively more proximal or more distal locations than shown on lead 16 to position emitting device 18 at a desired location relative to therapy delivery device 100.

Figure 2:
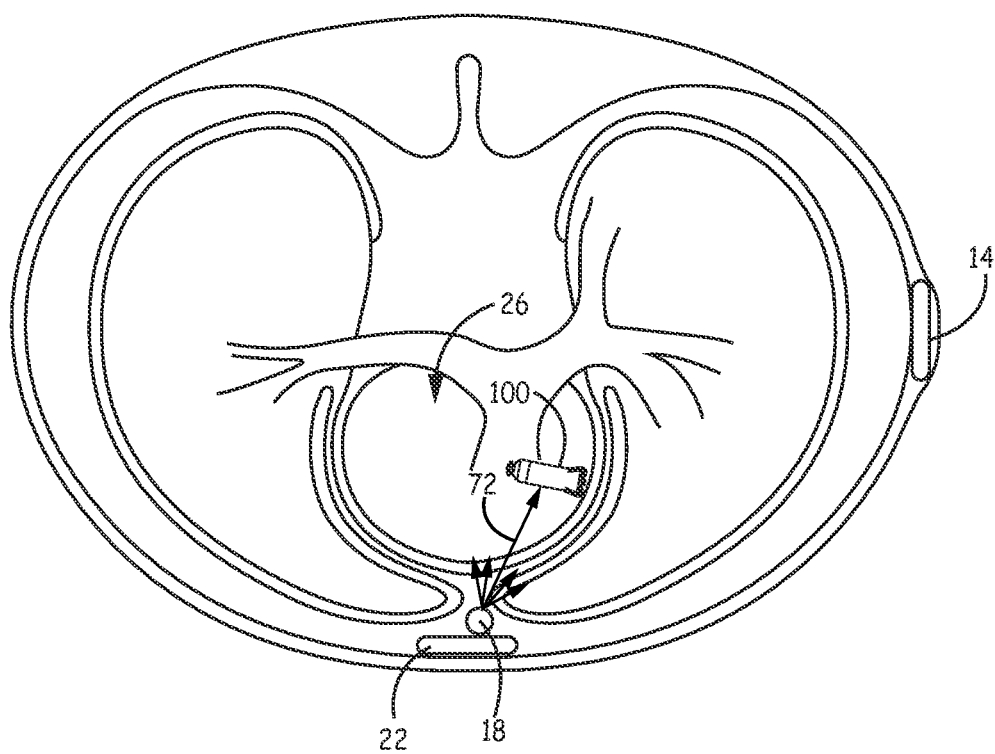
FIG. 2 is a sectional view of the patient's anatomy depicting an alternative configuration of the implantable medical device system of FIG. 1.

FIG. 2 is a sectional view of the patient's anatomy depicting an alternative configuration of the implantable medical device system of FIG. 1. Emitting device 18 is shown in a substernal position on lead 16 (not seen in the sectional view of FIG. 2). Instead of being positioned suprasternally, inferior to the xyphoid process, emitting device 18 may be positioned substernally and relatively more superior by advancing the distal end of lead 16 to a substernal location. Emitting device 18 may be configured for directional trigger signal emission with emitting device 18 oriented to generally direct the trigger signal toward the implant position of therapy delivery device 100, e.g., along a signal pathway to therapy delivery device 100 as represented by arrow 72.

Lead 16 may be placed under or below the sternum in the mediastinum and, more particularly, in the anterior mediastinum. The anterior mediastinum is bounded laterally by pleurae, posteriorly by pericardium, and anteriorly by sternum. Lead 16 may be at least partially implanted in other extra-pericardial locations, i.e., locations in the region around, but not necessarily in direct contact with, the outer surface of heart 26. These other extra-pericardial locations may include in the mediastinum but offset from sternum 22, in the superior mediastinum, in the middle mediastinum, in the posterior mediastinum, in the sub-xiphoid or inferior xiphoid area, near the apex of the heart, or other location not in direct contact with heart 26 and not subcutaneous. In other embodiments, lead 16 may extend within the pericardium and in direct contact with heart 26. In any of these illustrative implant locations, lead 16 may be positioned to optimally position trigger signal emitting device 18 for reliably transmitting a trigger signal to therapy delivery device 100.

Figure 3:
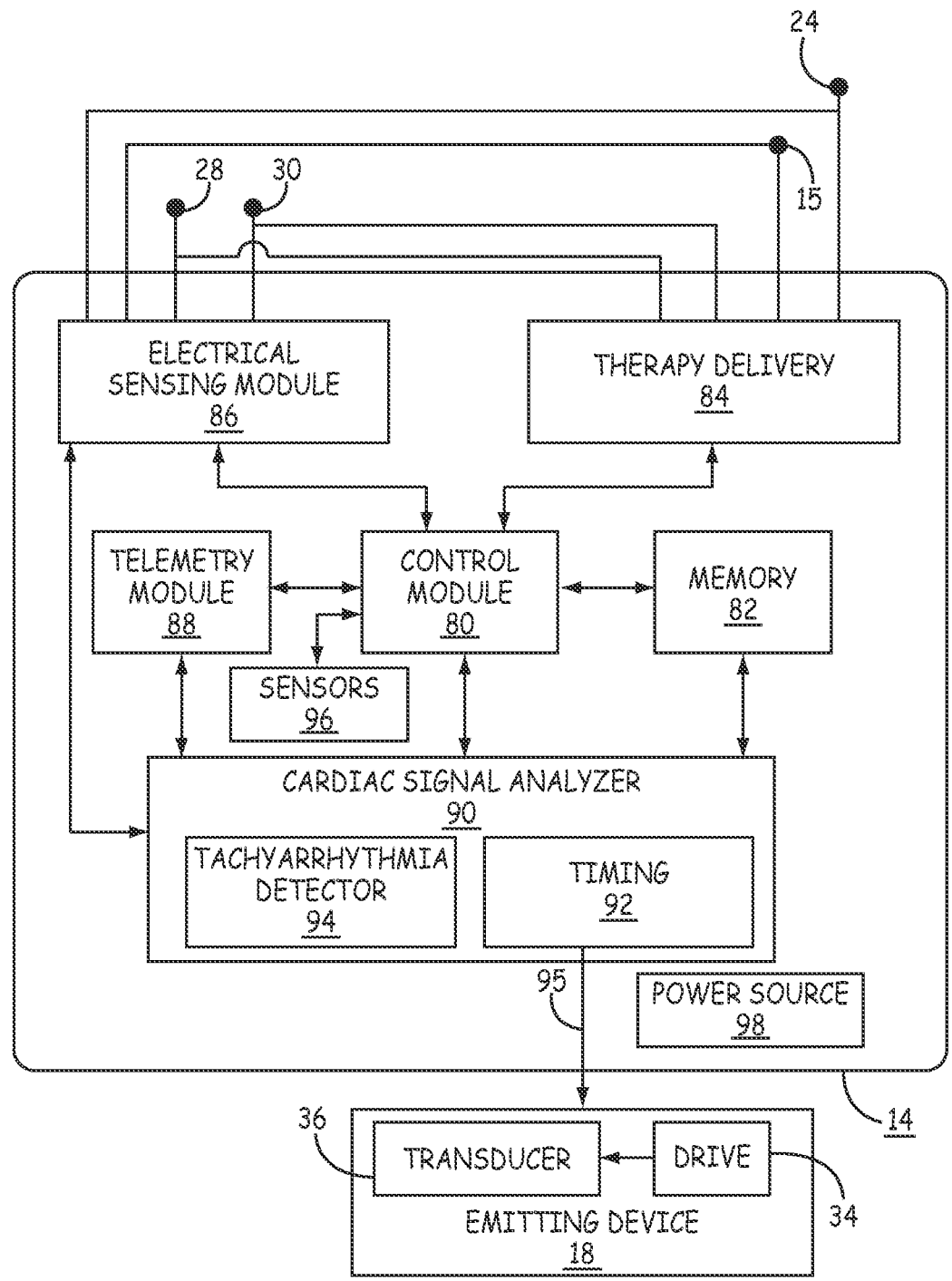
FIG. 3 is a functional block diagram of electronic circuitry that is included in one embodiment of the implantable medical device system shown in FIGS. 1 and 2.

FIG. 3 is a functional block diagram of electronic circuitry that is included in one embodiment of the implantable medical device system shown in FIGS. 1 and 2. As illustrated in FIG. 3, ICD 14 includes processing and control module 80, also referred to as "control module" 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, 90. Power source 98 may include one or more energy storage devices, such as one or more chargeable or non-re-chargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 and/or therapy delivery device 100 may be implemented in processing and control module 80 executing instructions stored in memory 82.

Processing and control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16, e.g., as shown in FIG. 1, and housing 15, at least a portion of which also serves as a common or ground electrode.

Electrical sensing module 86 is coupled to electrodes 28 and 30 in order to monitor electrical activity of the patient's heart. Electrical sensing module 86 may optionally be coupled to electrodes 24 and 15 and enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers included in sensing module 86. Switching circuitry may include a switch array, switch matrix, multiplexer, or any other type of switching device suitable to selectively couple sense amplifiers to selected electrodes. A sensing vector between electrodes 28 and 30 may be selected for sensing an ECG signal, although it is recognized that in some embodiments sensing vectors may be selected that utilize coil electrode 24 and/or housing electrode 15, e.g., from electrode 28 to housing 15 or electrode 30 and housing 15.

One or more ECG signals are received by an input of sensing module 86. Sensing module 86 includes one or more sense amplifiers or other cardiac event detection circuitry for sensing cardiac events, e.g., P-waves or R-waves, from the ECG signal(s). Sensing module 86 passes sense event signals to cardiac signal analyzer 90 in response to sensing cardiac events. For example P-wave sense event signals and R-wave sense event signals are passed to cardiac signal analyzer 90 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 92. In response to the pacing escape interval expiring, a control signal 95 is passed to the trigger signal emitting device 18. The pacing escape interval is restarted upon a trigger signal or a sense event signal.

The control signal 95 in the illustrative examples presented herein may be referred to as a pacing control signal because it causes therapy delivery device 100 to deliver a pacing pulse to a heart chamber. In other examples, the control signal 95 may be produced by cardiac signal analyzer 90 to cause other types of therapy pulses to be delivered by therapy delivery device 100 (or another therapy delivery device). For example control signal 95 may be produced to cause therapy delivery device 100 or another therapy delivery device to deliver an ATP pulse, a vagal nerve stimulation pulse, or other type of electrical stimulation pulse.

The control signal 95 is an electrical signal that is passed to emitting device 18 along lead 16 or 60 (or another lead carrying emitting device 18) when emitting device 18 is coupled to ICD 14 in a wired connection. The control signal 95 is alternatively a wireless telemetry signal that is transmitted via telemetry module 88, to emitting device 18. Emitting device 18 may be carried by a lead but configured to wirelessly receive a control signal 95 from telemetry module 88. Alternatively, the emitting device 18 is not a lead-based emitting device and receives control signal 95 wirelessly, e.g., as an RF telemetry signal, from telemetry module 88. It is understood that in some embodiments, drive signal circuit 34 may be included within the housing 15 of ICD 14 and coupled to transducer 36 located external to housing 15.

Trigger signal emitting device 18 includes a drive signal circuit 34 that receives the control signal 95, either as a wired electrical signal or a wireless signal from telemetry module 88. Drive signal circuit 34 passes an electrical signal to transducer 36 to enable transducer 36 to emit the trigger signal. Transducer 36 may be an optical transducer or an acoustical transducer in various examples. In other examples, the drive signal circuit 34 is coupled to an antenna for transmitting the trigger signal as an RF signal.

The trigger signal is received and detected by therapy delivery device 100 causing therapy delivery device 100 to deliver one or more pacing pulses to the patient's heart. In some examples, the trigger signal is generated according to predetermined frequency, amplitude, duration and other characteristics that are not intentionally varied by emitting device 18 under the control signal 95. In other words, the trigger signal merely signals therapy delivery device 100 to deliver therapy without any information relating to how many pacing pulses, what pulse amplitude or pulse width or other pacing pulse control parameters. Therapy delivery device 100 is programmed to deliver a predetermined number of pacing pulses according to predefined pulse control parameters when the trigger signal is detected.

Alternatively, control signal 95 may include encoded pacing pulse control information. The control signal 95 generated by drive circuit 34 may cause transducer 36 to emit a trigger signal according to a frequency, duration, amplitude or other intentionally varied characteristics of the trigger signal to include pacing pulse control parameter information. As described below, a parameter of the trigger signal emitted by transducer 36 may be controllably varied by control signal 95 and drive circuit 34 to cause therapy delivery device 100 to adjust a pacing pulse control parameter such as pacing pulse width, pulse number, etc. Trigger signal parameters that may be varied under the control of signal 95 and drive circuit 34 include, without limitation, trigger signal amplitude, signal frequency, pulse width, pulse number and interpulse interval.

Transducer 36 may be embodied as one or more transducers configured to emit sound or light, for example, upon receiving a drive signal from circuit 34. Transducer 36 may include any combination of one or more of a ceramic piezoelectric crystal, a polymer piezoelectric crystal, capacitive micromachined ultrasonic transducer (CMUT), piezoelectric micromachined ultrasonic transducer (PMUT), or other ultrasonic transducer, a light emitting diode (LED), a vertical cavity surface emitting laser (VCSEL) or other light source having a high quantum efficiency at a selected light wavelength. Transducer 36 may include multiple transducers arranged in an array and/or configured to emit signals in multiple directions from emitting device 18 to promote reception of the trigger signal by therapy delivery device 100 despite shifting, rotation or other changes of the relative orientations of emitting device 18 and therapy delivery device 100 with respect to each other. The multiple transducers may be selectable by drive circuit 34 such that a single one or combination of transducers producing the best signal-to-noise ratio at the pacemaker receiving transducer is selected.

In one example, transducer 36 may include multiple acoustic transducers activated by drive signal circuit 34 to emit sound waves that constructively interfere to improve the efficiency of acoustical signal transmission. Emitting device 18 is shown as a single device but may be implemented as more than one emitting device such that transmission of the trigger signal is distributed over two or more emitting devices. When two or more emitting devices are used, emitting device 18 may include one or more lead-based emitting devices, one or more leadless emitting devices, and/or one or more emitting devices incorporated in ICD 14. Two or more emitting devices may be activated synchronously to produce ultrasound waves that superimpose at the receiver of therapy delivery device 100 to increase transmission efficiency and/or improve signal reception. A phased array of transducers that can be independently pulsed to emit sound can be used to focus the acoustical signal toward the intended receiving transducer in therapy delivery device 100. When multiple therapy delivery devices 100 or other therapy delivery devices are included, a phased array of transducers included in transducer 36 may be controlled by drive signal circuit 34 to pulse the transducers in a programmed time relationship to focus the trigger signal on the receiver of an intended therapy delivery device.

Transducer 36 may include multiple transducers having different properties for emitting different frequencies of sound, light or RF signal. The different transducers are selectable by drive circuit 34 to enable transmission of different frequencies of trigger signals. For example, different frequencies or different patterns of amplitude, frequency, pulse number, etc. may be emitted for triggering different responses by therapy delivery device 100 or for triggering different intracardiac pacemakers when multiple pacemakers are implanted. As indicated above, different trigger signals may be used to cause therapy delivery device 100 to deliver pacing pulses according to different pacing pulse control parameters, such as different pulse shape, pulse amplitude, pulse width, pulse rate or pulse number.

The transducer 36 is configured to emit a trigger signal at an amplitude and frequency that is detectable by a receiving transducer of therapy delivery device 100, after attenuation by body tissues along the pathway between the transducer 36 and the therapy delivery device 100. In one example, transducer 36 is configured to emit sounds in the range of approximately 40 kHz to over 1 MHz. An optical trigger signal may be emitted with a wavelength greater than approximately 1000 nm. An RF signal can be radiated from an antenna at frequencies between 400 MHz and 3 GHz. The frequency of the trigger signal is selected in part based on the types and thicknesses of body tissues encountered along the signal pathway.

Timing circuit 92 may generate control signal 95 to trigger therapy delivery device 100 to provide bradycardia pacing, anti-tachycardia pacing, cardiac resynchronization therapy, AV nodal stimulation, or other pacing therapies according to pacing algorithms and timing intervals stored in memory 82. Bradycardia pacing may be delivered by therapy delivery device 100 temporarily to maintain cardiac output after delivery of a cardioversion-defibrillation shock by ICD 14 as the heart recovers back to normal function post-shock.

Cardiac signal analyzer 90 includes a tachyarrhythmia detector 94 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 (Greenhut, et al.), hereby incorporated herein by reference in its entirety. The timing of R-wave sense event signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized ECG signals to cardiac signal analyzer 90 for use in detecting tachyarrhythmia. Examples of ICDs that may be adapted for use with a triggered therapy delivery device 100 and operations that may be performed by tachyarrhythmia detector 94 for detecting, discriminating and treating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316 (Gillberg et al.), U.S. Pat. No. 5,545,186 (Olson, et al.), and U.S. Pat. No. 5,855,593 (Olson, et al.), all of which patents are incorporated herein by reference in their entirety.

The detection algorithms are highly sensitive and specific for the presence or absence of life threatening VT and VF. Therapy delivery module 84 includes a HV therapy delivery module including one or more HV output capacitors. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using coil electrode 24 and housing electrode 15.

It should be noted that implemented arrhythmia detection algorithms may utilize not only ECG signal analysis methods but may also utilize supplemental sensors 96, such as tissue color, tissue oxygenation, respiration, patient activity, heart sounds, and the like, for contributing to a decision by processing and control module 80 to apply or withhold a therapy. Sensors 96 may also be used in determining the need and timing for pacing by therapy delivery device 100. For example, an activity sensor signal or other rate responsive sensor signal, such as a minute ventilation signal, may be used for determining a pacing rate meeting a patient's metabolic demand. Timing circuit 92 produces a control signal 95 to cause emitting device 18 to generate trigger signals that cause therapy delivery device 100 to deliver pacing pulses at an appropriate rate based on the rate responsive signal. Sensors 96 may include one or more sensors carried by a lead extending from ICD 14 or within or along housing 15 and/or connector block 13.

Telemetry module 88 includes a transceiver and antenna for communicating with another device, such as an external programmer 40 and emitting device 18 when it is configured to receive control signal 95 wirelessly. Under the control of control module 80, telemetry module 88 may receive downlink telemetry from and send uplink telemetry to programmer 40 or another external device. Telemetry module 88 may transmit a control signal wirelessly to emitting device 18, e.g., as an RF signal.

Figure 4:
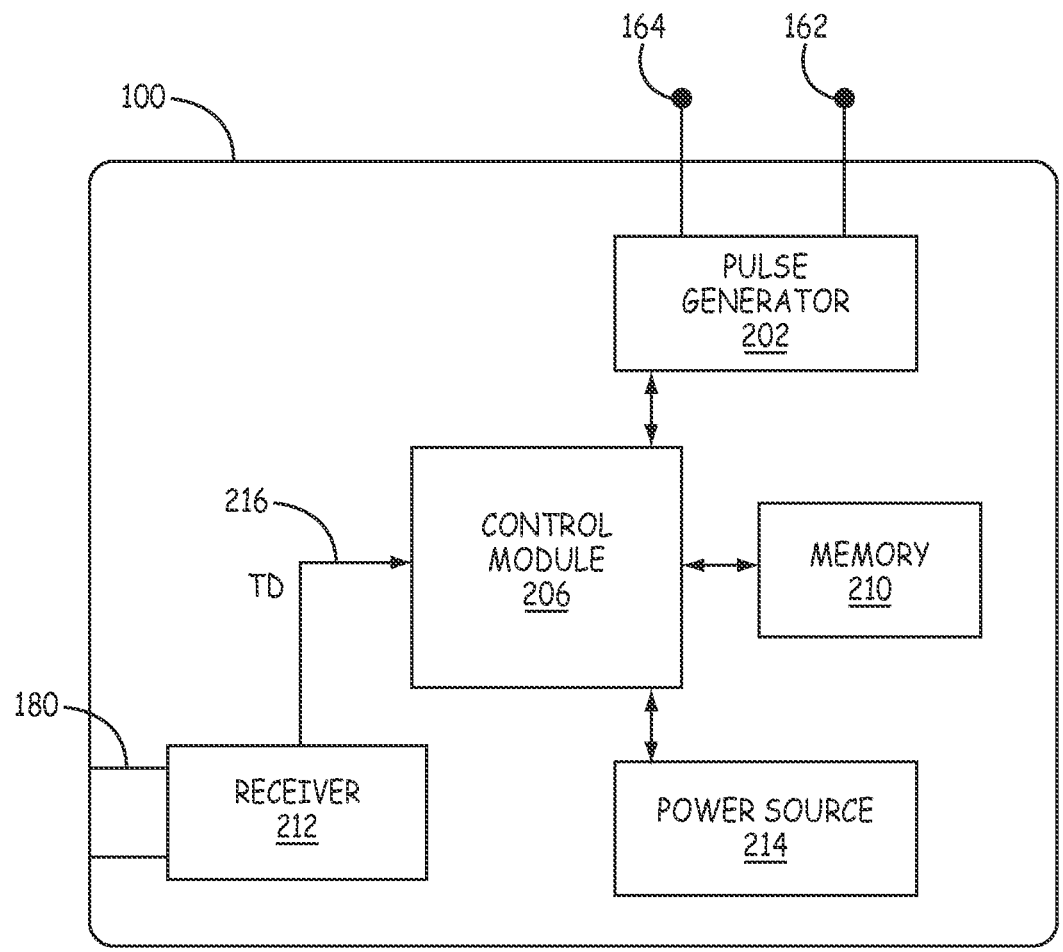
FIG. 4 is a functional block diagram of an example configuration of a therapy delivery device according to an embodiment of the present disclosure.

FIG. 4 is a functional block diagram of an example configuration of a therapy delivery device according to an embodiment of the present disclosure. As illustrated in FIG. 4, therapy delivery device 100 includes a pulse generator 202, an optional sensing module (not shown), a control module 206, memory 210, trigger signal receiver 212 and a power source 214. Pulse generator 202 generates electrical stimulation pulses that are delivered to heart tissue via electrodes 162 and 164. Control module 206 controls pulse generator 202 to deliver a stimulation pulse in response to receiving a trigger detect (TD) signal 216 from receiver 212. In other embodiments, pulse generator 202 may be configured to be enabled to deliver a stimulation pulse directly by an input signal received from receiver 212. For example, a switch responsive to a trigger detect signal 216 produced by receiver 212 may enable pulse generator 202 to deliver a stimulation pulse to a targeted tissue via electrodes 162 and 164.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from receiver 212. Upon detecting the trigger signal, the capacitor is coupled to pacing electrodes 162, 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in therapy delivery device 100 for charging a pacing capacitor to a predetermined pacing pulse amplitude under the control of control module 206 and delivering a pacing pulse.

Alternatively, pulse generator 202 may include a switch that connects power source 214 to pacing electrodes 162 and 164 to deliver the pacing pulse. The switch is opened by trigger detect signal 216 or by a control signal from control module 206, and power source 214 delivers energy to pulse generator 202 for generating a pacing pulse.

As described below, control module 206 may determine a pacing pulse control parameter from the trigger detect signal 216 and use the determined pacing pulse control parameter to control pulse generator 202 to deliver one or more pacing pulses in accordance with the determined control parameter. For example, the pulse width or other aspect of the trigger signal may be determined by control module 206 and used to set the pulse width (or another aspect) of the pacing pulse.

Receiver 212 receives trigger signals through coupling member 180. Receiver 212 includes one or more receiving transducers, which may be mounted directly along an inner surface of coupling member 180, e.g., for receiving sound waves or light. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal 216 is passed to control module 206, or directly to pulse generator 202, to cause pacing pulse delivery.

The receiver 212 is configured to detect only the emitting device-generated trigger signal in some embodiments. For example, receiver 212 may be "tuned" to detect an acoustical or optical signal of a particular signal frequency or bandwidth that is outside a normal physiological range of acoustical or optical signal sensing. In some examples, receiver 212 is not configured to sense and process any physiological acoustical signals or optical signals for determining a physiological event, condition or state.

Control module 206 controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving a trigger detect signal 216, either directly from receiver 212 or via control module 206. Alternatively, the pacing pulse may be delivered after a predetermined time delay.

Receiver 212 may include multiple receiving transducers for sensing the trigger signal. The voltage signal produced by multiple transducers may be summed, for example, for comparison to a trigger signal detection threshold. In some embodiments, multiple receiving transducers may be included that are responsive to different frequency bandwidths. Providing detection of different signal frequencies may enable different trigger signals to be transmitted for causing therapy delivery device 100 to perform different pacing functions and/or improve trigger signal detection.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries.

Circuitry represented by the block diagram shown in FIG. 4 may include any discrete and/or integrated electronic circuit components that implement analog and/or digital circuits capable of producing the functions attributed to therapy delivery device 100 herein. The functions attributed to therapy delivery device 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of therapy delivery device 100 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to therapy delivery device 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal received by receiver 212.

Figure 5:
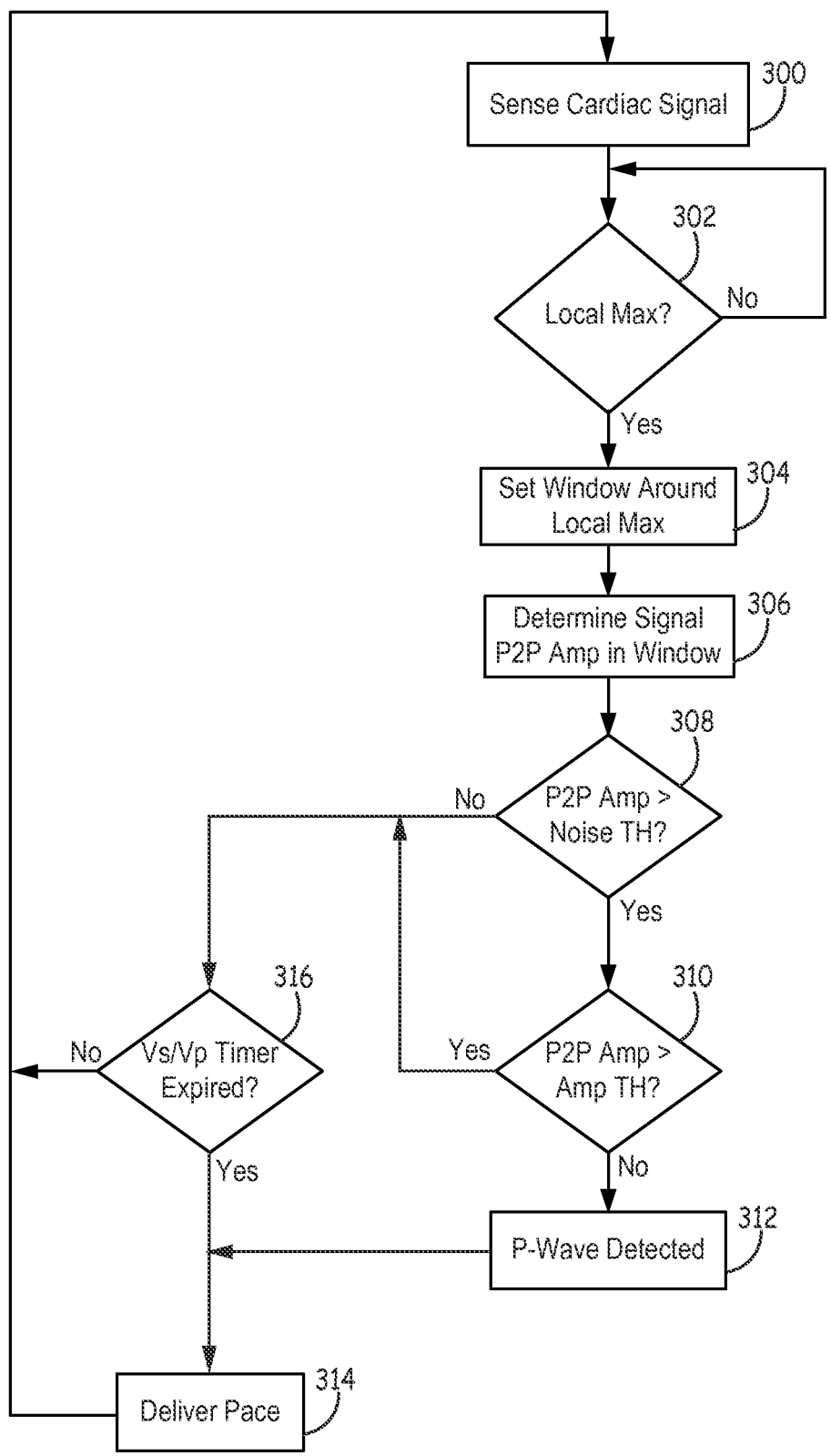
FIG. 5 is a flowchart of a method for controlling delivery of a pacing therapy in a medical device and medical device system, according to an embodiment of the present disclosure.

FIG. 5 is a flowchart of a method for controlling delivery of pacing therapy in a medical device and medical device system, according to an embodiment of the present disclosure. As illustrated in FIG. 5, according to an embodiment of the present disclosure, in order to reduce the time required to confirm the occurrence of a P-wave during delivery of a ventricular pacing therapy, the sensing device 14 senses the cardiac signal, Block 300, via one or more sensing vectors that include combinations of electrodes 28 and 30 and housing 15 (shown in FIG. 1) and determines, during real-time sensing of the cardiac signal, whether a local maximum of the cardiac signal occurs, Block 302.

According to one embodiment, in order to identify the occurrence of a local maximum of the cardiac signal, the device senses the signal and determines when a change in the sign of the slope of the real-time signal occurs, or uses a derivative signal, for example, and identifies the point of zero slope as a local maximum of the signal, Yes in Bock 302. Once the local maximum is identified, the device sets a window around the local maximum, Block 304, having a start point located a predetermined distance prior to the local maximum and an endpoint located another predetermined distance subsequent to the local maximum of the signal and that is less than the predetermined distance prior to the local maximum. The distance that the endpoint is positioned relative to the local maximum of the signal may be 40 ms, 50 ms, 60 ms, 70 ms, 75 ms or 80 ms, for example, and the distance that the start point is positioned relative to the local maximum of the signal may be 120 ms, 100 ms 80 ms, 60 ms and 50 ms, for example. In any case, the distance that the endpoint is positioned relative to the local maximum is set to be less than or equal to the distance that the start point is positioned relative to the local maximum, and the total width of the window, would be a distance extending from the start point to the endpoint for between 100 and 200 ms. According to one embodiment, the window start point is located 120 ms prior to the local maximum and the window endpoint is located 40 ms after the local maximum.

It is understood that fiducials other than a local maximum may be utilized to set the window start point and the window endpoint, including, for example, a local minimum or a predetermined threshold crossing of the slope or the rectified slope (slew rate) of the cardiac signal.

Once the window is set, block 304, the device determines a peak-to-peak (P2P) amplitude of the signal within the window, Block 306, and determines whether the peak-to-peak amplitude is greater than a noise threshold, Block 308. If the peak-to-peak amplitude is greater than a noise threshold, Yes in Block 308, the device determines whether the peak-to-peak amplitude is greater than amplitude threshold, Block 310. If the peak-to-peak amplitude is not greater than the amplitude threshold, No in Block 310, i.e., the peak-to peak amplitude is less than the amplitude threshold, the device detects the local maximum as being a P-wave, Block 312, and delivers the ventricular pace Block 314, with the delivery being timed off of the local maximum using a pre-specified atrio-ventricular (AV) interval.

The noise threshold of Block 308 and the amplitude threshold of Block 310 define a lower limit and an upper limit, which may be set based on P-wave amplitudes collected by the device based on prior determined signal peak-to-peak amplitudes corresponding to expected occurrences of P-waves, sensed a predetermined distance before ventricular sensing when the device was not in a pacing mode, such as between 80 ms and 200 ms prior to the ventricular sensing of the non-paced signal, for example. In this way, the device detects the local maximum as a P-wave if the local maximum is greater than a noise signal but less than the amplitude threshold, thereby reducing the likelihood of being a T-wave signal, an R-wave signal or premature ventricular contractions (PVCs).

If it is determined that the local maximum not greater than the noise signal threshold, No in Block 308, the local maximum is determined to be associate with noise, and a determination is made as to whether a timer, associated with a desired AV interval associated with the timing of ventricular pacing pulses relative to a preceding atrial depolarization, intrinsic or paced, has expired, Block 316. If the timer has expired, Yes in Block 316, the device delivers ventricular pace Block 314, with the delivery not being timed off of the local maximum. In the same way, if it is determined that the local maximum greater than the amplitude threshold, Yes in Block 310, the local maximum is determined to be associate with either a T-wave, an R-wave or premature ventricular contractions (PVCs), and a determination is made as to whether a timer, associated with a desired AV interval associated with the timing of ventricular pacing pulses relative to a preceding atrial depolarization, intrinsic or paced, has expired, Block 316. If the timer has expired, Yes in Block 316, the device delivers a ventricular pacing therapy, Block 314, with the delivery not being timed off of the local maximum. If the timer has not expired, No in Block 316, the device continues sensing the far-field ECG/EGM signal, Block 300, and the process is repeated.

Figure 6:
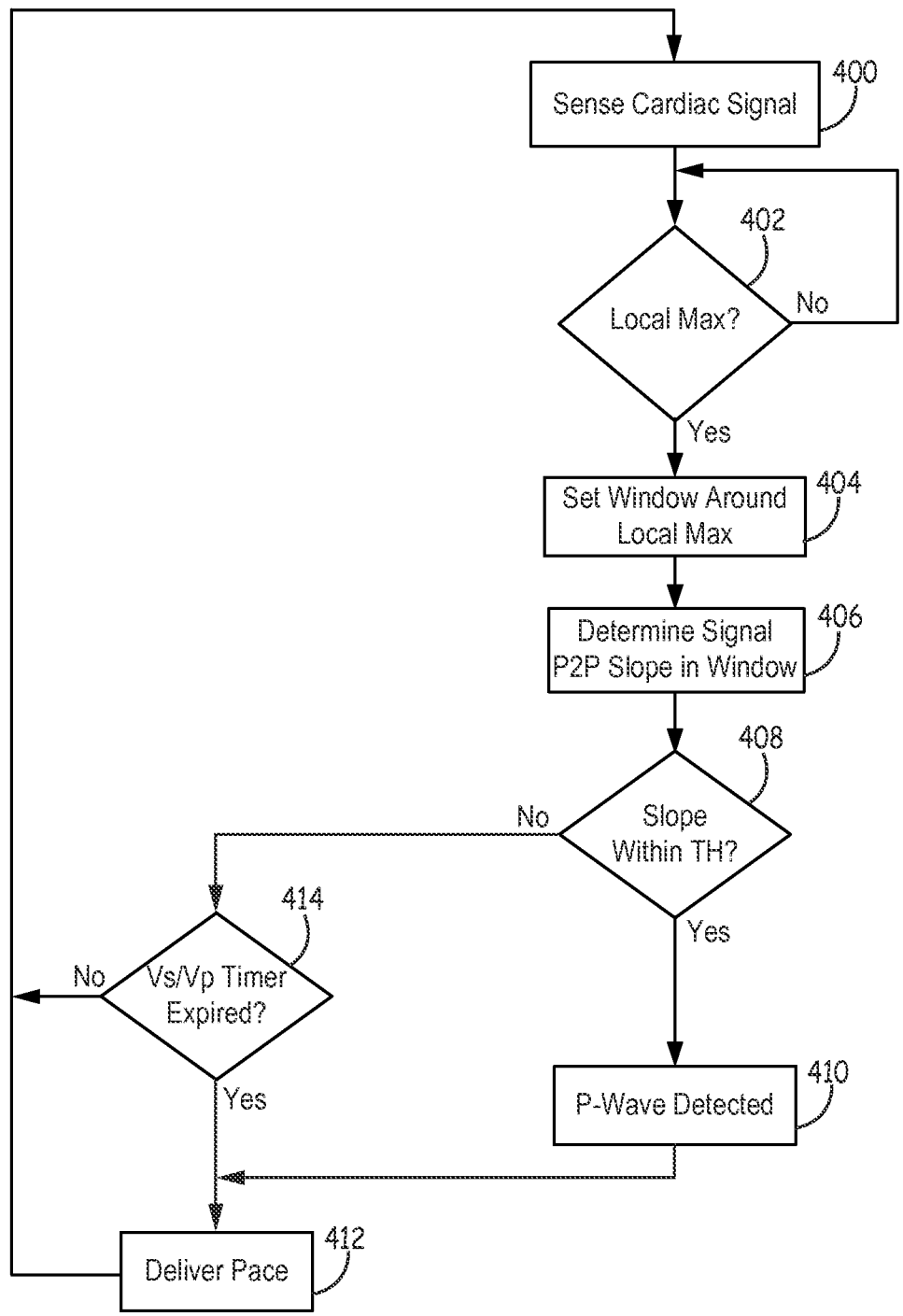
FIG. 6 is a flowchart of a method for controlling delivery of a pacing therapy in a medical device and medical device system, according to an embodiment of the present disclosure.

FIG. 6 is a flowchart of a method for controlling delivery of a pacing therapy in a medical device and medical device system, according to an embodiment of the present disclosure. As illustrated in FIG. 6, according to another embodiment of the present disclosure, the sensing device 14 senses the cardiac signal, Block 400, via one or more sensing vectors that include combinations of electrodes 28 and 30 and housing 15 (shown in FIG. 1) and determines, during reral-time sensing of the cardiac signal, when a local maximum of the cardiac signal occurs, Block 402. According to one embodiment, in order to identify the occurrence of a local maximum of the cardiac signal, the device senses the signal and determines when a change in in the sign of the slope of the real-time signal occurs, or uses a derivative signal, for example, and identifies the point of zero slope as a local maximum of the signal, Yes in Bock 402. Once the local maximum is identified, the device sets a window around the local maximum, Block 404, having a start point located a predetermined distance prior to the local maximum and an endpoint located another predetermined distance from the local maximum of the signal. The distance that the endpoint is positioned relative to the local maximum of the signal may be 40 ms, 50 ms, 60 ms, 70 ms, 75 ms or 80 ms, for example, and the distance that the start point is positioned relative to the local maximum of the signal may be 120 ms, 100 ms 80 ms, 60 ms and 50 ms, for example. In any case, the distance that the endpoint is positioned relative to the local maximum is set to be less than or equal to the distance that the start point is positioned relative to the local maximum, and the total width of the window, would be a distance extending from the start point to the endpoint for between 100 and 200 ms. For example, according to one embodiment, the window start point is located 120 ms prior to the local maximum and the window endpoint is located 40 ms after the local maximum.

Once the window is set, block 404, the device determines a peak-to-peak slope of the signal within the window, Block 406, and determines whether the peak-to-peak slope is within a slope threshold, Block 408. Exemplary values of the lower limits of the slope threshold may be 0.05-0.1 mV/ms and the upper limit may be 0.1-1.0 mV/ms, for example. In another embodiment the lower and upper limits of the slope threshold may be determined based on the history of the maximum and minimum slopes determined by retrospective computation of maximum and minimum slopes of signals within a window that starts 200 ms before a ventricular sense event and ends 50 ms before the ventricular sense event. If the peak-to-peak slope is within the slope threshold, Yes in Block 408, the device detects the local maximum as being a P-wave, Block 410, and delivers the ventricular pace, Block 412, with the delivery being timed off of the local maximum.

If it is determined that the local maximum is not within the slope threshold, No in Block 408, a determination is made as to whether a timer, associated with a desired AV interval associated with the timing of ventricular pacing pulses relative to a preceding atrial depolarization, intrinsic or paced, has expired, Block 414. If the timer has expired, Yes in Block 414, the device delivers the ventricular pace Block 412, with the delivery not being timed off of the local maximum. If the timer has not expired, No in Block 414, the device continues sensing the cardiac signal, Block 400, and the process is repeated.

Figure 7:
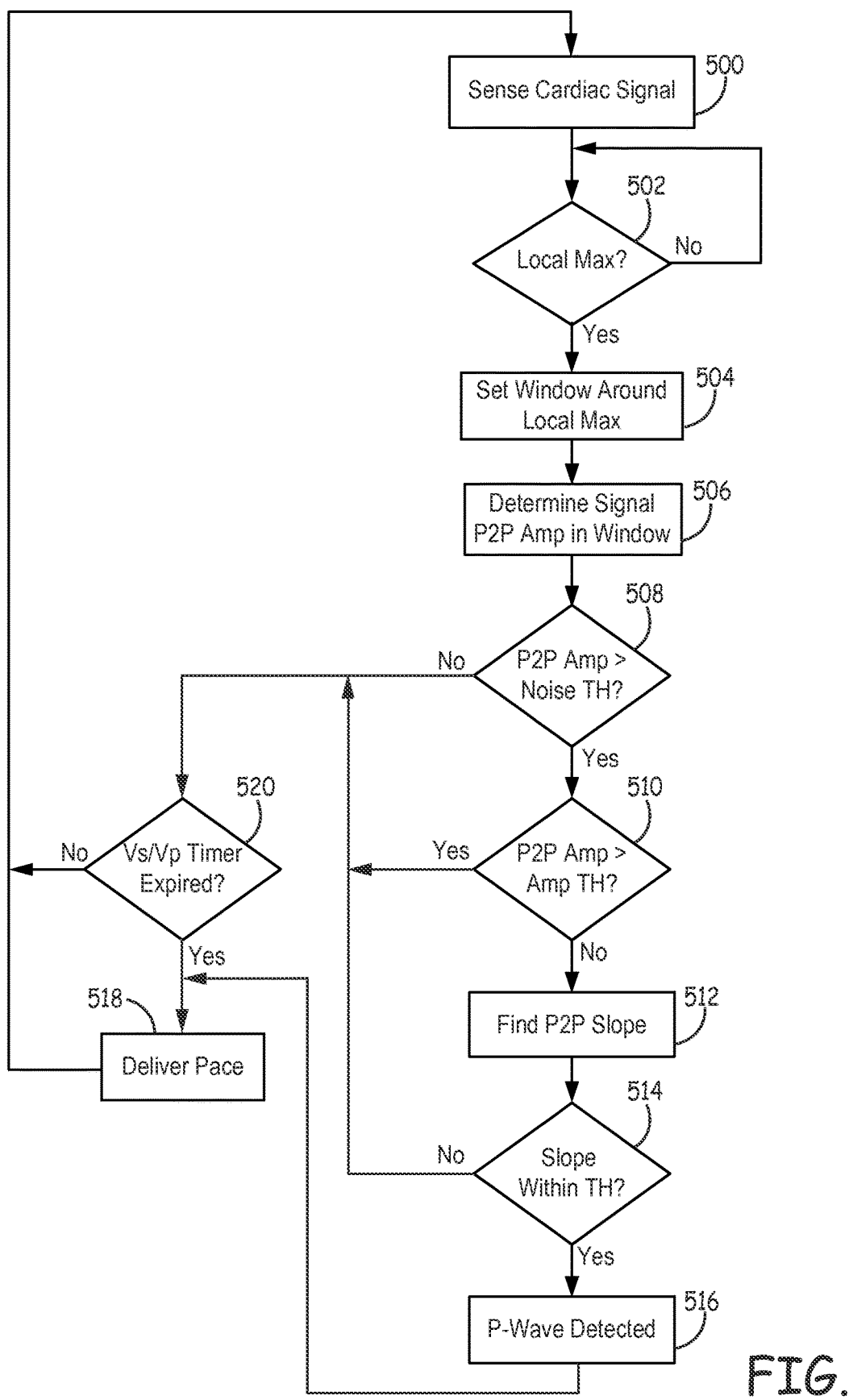
FIG. 7 is a flowchart of a method for controlling delivery of a pacing therapy in a medical device and medical device system, according to an embodiment of the present disclosure.

FIG. 7 is a flowchart of a method for controlling delivery of a pacing therapy in a medical device and medical device system, according to an embodiment of the present disclosure. As illustrated in FIG. 7, according to another embodiment of the present disclosure, the sensing device 14 senses the cardiac signal, Block 500, via one or more sensing vectors that include combinations of electrodes 28 and 30 and housing 15 (shown in FIG. 1) and determines, during real-time sensing of the cardiac signal, when a local maximum of the cardiac signal occurs, Block 502. According to one embodiment, in order to identify the occurrence of a local maximum of the cardiac signal, the device senses the signal and determines when a change in the sign of the slope of the real-time signal occurs, or uses a derivative signal, for example, and identifies the point of zero slope as a local maximum of the signal, Yes in Bock 502. Once the local maximum is identified, the device sets a window around the local maximum, Block 504, having a start point located a predetermined distance prior to the local maximum and an endpoint located another predetermined distance from the local maximum of the signal. The distance that the endpoint is positioned relative to the local maximum of the signal may be 40 ms, 50 ms, 60 ms, 70 ms, 75 ms or 80 ms, for example, and the distance that the start point is positioned relative to the local maximum of the signal may be 120 ms, 100 ms 80 ms, 60 ms and 50 ms, for example. In any case, the distance that the endpoint is positioned relative to the local maximum is set to be less than or equal to the distance that the start point is positioned relative to the local maximum, and the total width of the window, would be a distance extending from the start point to the endpoint for between 100 and 200 ms. For example, according to one embodiment, the window start point is located 120 ms prior to the local maximum and the window endpoint is located 40 ms after the local maximum.

Once the window is set, block 504, the device determines whether the peak-to-peak amplitude is greater than a noise threshold, Block 508. If the peak-to-peak amplitude is greater than a noise threshold, Yes in Block 508, the device determines whether the peak-to-peak amplitude is greater than an amplitude threshold, Block 510. If the peak-to-peak amplitude is not greater than the amplitude threshold, No in Block 510, i.e., the device determines a peak-to-peak slope of the signal within the window, Block 512, and determines whether the peak-to-peak slope is within a slope threshold, Block 514. If the peak-to-peak amplitude is within the slope threshold, Yes in Block 514, the device detects the local maximum as being a P-wave, Block 516, and delivers the ventricular pace, Block 518, with the delivery being timed off of the local maximum using a predetermined atrio-ventricular (AV) interval.

If it is determined that the local maximum not greater than the noise signal threshold, No in Block 508, the local maximum is determined to be associate with noise, and a determination is made as to whether a timer, associated with a desired AV interval associated with the timing of ventricular pacing pulses relative to a preceding atrial depolarization, intrinsic or paced, has expired, Block 520. If the timer has expired, Yes in Block 520, the device delivers ventricular pace Block 518, with the delivery not being timed off of the local maximum. If it is determined that the local maximum greater than the amplitude threshold, Yes in Block 510, the local maximum is determined to be associate with either a T-wave, an R-wave, or a premature ventricular contraction (PVC) and a determination is made as to whether a timer, associated with a desired AV interval associated with the timing of ventricular pacing pulses relative to a preceding atrial depolarization, intrinsic or paced, has expired, Block 520. If the timer has expired, Yes in Block 520, the device delivers ventricular pace Block 518, with the delivery not being timed off of the local maximum using a predetermined atrio-ventricular (AV) interval. If the timer has not expired, No in Block 520, the device continues sensing the cardiac signal, Block 500, and the process is repeated.

In the same way if it is determined that the local maximum is not within the slope threshold, No in Block 514, a determination is made as to whether a timer, associated with a desired AV interval associated with the timing of ventricular pacing pulses relative to a preceding atrial depolarization, intrinsic or paced, has expired, Block 520. If the timer has expired, Yes in Block 520, the device delivers the ventricular pace Block 518, with the delivery not being timed off of the local maximum. If the timer has not expired, No in Block 520, the device continues sensing the cardiac signal, Block 500, and the process is repeated.

The techniques described in this disclosure, including those attributed to the IMD, the programmer, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A medical device system for controlling delivery of a ventricular pacing therapy during cardiac resynchronization therapy, comprising:
    a sensing device configured to sense a cardiac signal and to emit a trigger signal in response to the sensed cardiac signal;
    a therapy delivery device to receive the trigger signal and deliver the ventricular pacing to the patient in response to the emitted trigger signal; and
    a processor positioned within the sensing device, the processor configured to identify a fiducial point of the cardiac signal sensed in real-time, set a window comprising a start point positioned a first distance prior to the fiducial point and an endpoint positioned a second distance subsequent to the fiducial point, the second distance being less than the first distance, determine a signal characteristic of the cardiac signal within the window, determine whether a P-wave is detected in response to the signal characteristic, determine whether a timer associated with an atrio-ventricular interval has expired, and emit a trigger signal via the sensing device, the trigger signal being received by the therapy delivery device and instructing the therapy delivery device to deliver the ventricular pacing timed off of a local maximum in response to the P-wave being detected and not timed off of the local maximum in response to the timer being expired.

2. The medical device system of claim 1, wherein the processor is configured to determine a change in slope of the cardiac signal, and determine a local maximum of the cardiac signal as the fiducial point.

3. The medical device system of claim 1, wherein the processor is configured to determine a peak-to-peak amplitude of the cardiac signal within the window, determine whether the peak-to-peak amplitude is within a slope threshold, determine the P-wave is present in response to the peak-to-peak slope being within the slope threshold, and determining whether the timer has expired in response to the peak-to-peak slope not being within the slope threshold.

4. The medical device system of claim 1, wherein the processor is configured to determine a peak-to-peak amplitude of the cardiac signal within the window, determine whether the peak-to-peak amplitude is greater than a noise threshold, determine whether the peak-to-peak amplitude is greater than an amplitude threshold, determine whether the peak-to-peak amplitude is within a slope threshold, determine the P-wave is present in response to the peak-to-peak amplitude being greater than the noise threshold, the peak-to-peak amplitude not being greater than the amplitude threshold, and the peak-to-peak slope being within the slope threshold, and determining whether the timer has expired in response to one of the peak-to-peak amplitude not being greater than the noise threshold, the peak-to-peak amplitude being greater than the amplitude threshold, and the peak-to-peak slope not being within the slope threshold.

5. The medical device system of claim 4, wherein the processor is configured to determine a change in slope of the cardiac signal, and determine a local maximum of the cardiac signal as the fiducial point.

6. The medical device system of claim 1, wherein the sensing device comprises a subcutaneously implanted leadless device.

7. The medical device system of claim 1, wherein the first distances comprises 120 ms and the second distance comprised 40 ms.

8. A medical device system for controlling delivery of a ventricular pacing therapy during cardiac resynchronization therapy, comprising:
  a subcutaneous sensing device capable of being implanted subcutaneously within a patient configured to sense a cardiac signal and to emit a trigger signal in response to the sensed cardiac signal;
  subcutaneously implanted electrodes position along the sensing device configured to sense the cardiac signal;
  a therapy delivery device comprising a transcatheter intracardiac pacemaker adapted for implantation wholly within a heart chamber to receive the trigger signal and deliver the ventricular pacing to the patient in response to the emitted trigger signal; and
  a processor positioned within the sensing device, the processor configured to identify a fiducial point of the cardiac signal sensed in real-time, set a window comprising a start point positioned a first distance prior to the fiducial point and an endpoint positioned a second distance subsequent to the fiducial point, the second distance being less than the first distance, determine a signal characteristic of the cardiac signal within the window, determine whether a P-wave is detected in response to the signal characteristic, determine whether a timer associated with an atrio-ventricular interval has expired, and emit a trigger signal via the sensing device, the trigger signal being received by the therapy delivery device and instructing the therapy delivery device to deliver the ventricular pacing timed off of a local maximum in response to the P-wave being detected and not timed off of the local maximum in response to the timer being expired.

9. The medical device system of claim 8, wherein the processor is configured to determine a change in slope of the cardiac signal, and determine a local maximum of the cardiac signal as the fiducial point.

10. The medical device system of claim 8, wherein the processor is configured to determine a peak-to-peak amplitude of the cardiac signal within the window, determine whether the peak-to-peak amplitude is within a slope threshold, determine the P-wave is present in response to the peak-to-peak slope being within the slope threshold, and determining whether the timer has expired in response to the peak-to-peak slope not being within the slope threshold.

11. The medical device system of claim 8, wherein the processor is configured to determine a peak-to-peak amplitude of the cardiac signal within the window, determine whether the peak-to-peak amplitude is greater than a noise threshold, determine whether the peak-to-peak amplitude is greater than an amplitude threshold, determine whether the peak-to-peak amplitude is within a slope threshold, determine the P-wave is present in response to the peak-to-peak amplitude being greater than the noise threshold, the peak-to-peak amplitude not being greater than the amplitude threshold, and the peak-to-peak slope being within the slope threshold, and determining whether the timer has expired in response to one of the peak-to-peak amplitude not being greater than the noise threshold, the peak-to-peak amplitude being greater than the amplitude threshold, and the peak-to-peak slope not being within the slope threshold.

12. The medical device system of claim 11, wherein the processor is configured to determine a change in slope of the cardiac signal, and determine a local maximum of the cardiac signal as the fiducial point.

13. The medical device system of claim 11, wherein the first distances comprises 120 ms and the second distance comprised 40 ms.

14. A medical device system for controlling delivery of a ventricular pacing during cardiac resynchronization therapy, comprising:
  a subcutaneous sensing device comprising subcutaneously implanted electrodes configured to sense a cardiac signal and an emitting device to emit a trigger signal to deliver the therapeutic stimulation pulses in response to the sensed cardiac signal; and
  a processor positioned within the subcutaneous sensing device, the processor configured to identify a fiducial point of the cardiac signal sensed in real-time, set a window comprising a start point positioned a first distance prior to the fiducial point and an endpoint positioned a second distance subsequent to the fiducial point, the second distance being less than the first distance, determine a signal characteristic of the cardiac signal within the window, determine whether a P-wave is detected in response to the signal characteristic, determine whether a timer associated with an atrio-ventricular interval has expired, and emit a trigger signal via the sensing device, the trigger signal being received by the therapy delivery device and instructing the therapy delivery device to deliver the ventricular pacing timed off of a local maximum in response to the P-wave being detected and not timed off of the local maximum in response to the timer being expired.

15. The medical device system of claim 14, wherein the processor is configured to determine a change in slope of the cardiac signal, and determine a local maximum of the cardiac signal as the fiducial point.

16. The medical device system of claim 14, wherein the processor is configured to determine a peak-to-peak amplitude of the cardiac signal within the window, determine whether the peak-to-peak amplitude is within a slope threshold, determine the P-wave is present in response to the peak-to-peak slope being within the slope threshold, and determining whether the timer has expired in response to the peak-to-peak slope not being within the slope threshold.

17. The medical device system of claim 14, wherein the processor is configured to determine a peak-to-peak amplitude of the cardiac signal within the window, determine whether the peak-to-peak amplitude is greater than a noise threshold, determine whether the peak-to-peak amplitude is greater than an amplitude threshold, determine whether the peak-to-peak amplitude is within a slope threshold, determine the P-wave is present in response to the peak-to-peak amplitude being greater than the noise threshold, the peak-to-peak amplitude not being greater than the amplitude threshold, and the peak-to-peak slope being within the slope threshold, and determining whether the timer has expired in response to one of the peak-to-peak amplitude not being greater than the noise threshold, the peak-to-peak amplitude being greater than the amplitude threshold, and the peak-to-peak slope not being within the slope threshold.

18. The medical device system of claim 17, wherein the processor is configured to determine a change in slope of the cardiac signal, and determine a local maximum of the cardiac signal as the fiducial point.

19. The medical device system of claim 17, wherein the first distances comprises 120 ms and the second distance comprised 40 ms.

* * * * *